UNITED STATES PATENT OFFICE.

LEE E. H. CONE, OF MIDLAND, MICHIGAN, ASSIGNOR TO THE DOW CHEMICAL COMPANY, OF MIDLAND, MICHIGAN, A CORPORATION OF MICHIGAN.

METHOD OF MAKING INDOXYL AND DERIVATIVES.

14,364. Specification of Reissued Letters Patent. Reissued Sept. 25, 1917.

No Drawing. Original No. 1,211,413, dated January 9, 1917, Serial No. 105,078, filed June 21, 1916. Application for reissue filed June 18, 1917. Serial No. 175,500.

*To all whom it may concern:*

Be it known that I, LEE E. H. CONE, a citizen of the United States, and a resident of Midland, county of Midland, and State of Michigan, have invented a new and useful Improvement in Methods of Making Indoxyl and Derivatives, of which the following is a specification, the principle of the invention being herein explained and the best mode in which I have contemplated applying that principle, so as to distinguish it from other inventions.

Heumann himself developed an improvement in his original process for making indoxyl from phenyl-glycin or phenyl-glycocol, such improvement consisting in the use, instead of caustic soda or caustic potash alone or mixed with one another, of either or both of these alkalis admixed with quicklime (see U. S. Patent 617,652). The expected effect of such addition of the quicklime was apparently to secure a higher yield of the desired indoxyl. With this same object in view, it has also been proposed to admix with the caustic alkalis used in treating the phenyl-glycin, a small proportion of metallic sodium or an equivalent proportion of another alkali metal (see British Patent No. 26,061 of 1901). Still another method for accomplishing this result is to add an alkaline oxid, specifically sodium oxid, to the melt (see U. S. Patents Nos. 727,270 and 756,171).

I have found upon attempting to utilize the foregoing alleged improved processes, that none gives satisfactory results, and that the yield of indoxyl, even under the most careful manipulation, still falls short of that theoretically possible. I have discovered, however, that much more satisfactory results are obtained, where instead of adding either quicklime alone or such metallic alkali alone, to the melt of caustic alkalis, both of these ingredients are added.

My improved process, characterized by the feature just explained, consists of the steps hereinafter fully described and particularly pointed out in the claims, the following description setting forth only one method of carrying out my improved process and it being understood that various changes may be made therein, all within the scope of the invention.

In carrying out my improved process as indicated, I first prepare a so-called "melt" of caustic alkalis consisting preferably of both potassium hydroxid and sodium hydroxid, and then add thereto a quantity of quicklime, together with a smaller quantity of metallic sodium. These admixed ingredients are fused together under conditions which leave the metallic sodium present as such, and in this condition of the "melt" a quantity of a suitable phenyl-glycin body, as for example, phenyl-glycin potassium salt, is added thereto. The whole is maintained at a temperature of 250° C. for a half-hour or so, or until the reaction is complete. The mass while still fused or molten is then poured or run into water, out of contact with air, whereupon the indoxyl goes into solution.

As a specific example for the carrying out of the foregoing described process, I take 60 parts of potassium hydroxid and 40 parts of sodium hydroxid, which gives a low melting point mixture, adding thereto 15 parts of the quicklime, and 3 parts of metallic sodium. The mixture thus produced is adapted to react with 15 parts of the phenyl-glycin potassium salt.

It will be understood that in place of the specified quicklime, other alkaline-earth oxids, for example, strontium oxid or barium oxid, may be employed with satisfactory results. It is essential, however, according to my process that the metallic sodium be present as such in the fused mass, or melt, to which the phenyl-glycin body is added. It will, however, entirely disappear during the reaction with the latter, none remaining in the resultant product, if the proportion of each metal be properly chosen.

The foregoing improved process has been found in practice to give an entirely satisfactory yield of indoxyl, namely, from 65 to 75 per cent. of that which should be secured according to the theory of the reaction.

Other modes of applying the principle of my invention may be employed instead of the one explained, change being made as regards the process herein disclosed, provided the step or steps stated by any one of the following claims or the equivalent of such stated step or steps be employed.

I therefore particularly point out and distinctly claim as my invention:—

1. In a method of making indoxyl and its derivatives, the step which consists in heating a phenyl-glycin body with a mixture of caustic alkali, alkaline-earth oxid and metallic sodium present as such, substantially as set forth.

2. In a method of making indoxyl and its derivatives, the step which consists in heating a phenyl-glycin body with a mixture of potassium hydroxid, lime and metallic sodium present as such, substantially as set forth.

3. In a method of making indoxyl and its derivatives, the step which consists in heating a phenyl-glycin body with a mixture of sodium and potassium hydroxids, lime and metallic sodium present as such, substantially as set forth.

4. In a method of making indoxyl and its derivatives, the steps which consist in first fusing together caustic alkali, alkaline-earth oxid and metallic sodium, the latter remaining present as such; and then adding a phenyl-glycin body to such mixture.

5. In a method of making indoxyl and its derivatives, the steps which consist in fusing together a phenyl-glycin body with a mixture of caustic alkali, alkaline-earth oxid and metallic sodium present as such; and then passing the resulting product, while still in fused state, into water.

6. In a method of making indoxyl and its derivatives, the steps which consist in fusing together a phenyl-glycin body with a mixture of caustic alkali, alkaline-earth oxid and metallic sodium present as such; and then passing the resulting product, while still in fused state, into water, out of contact with air.

7. In a method of making indoxyl and its derivatives, the steps which consist in first fusing together caustic alkali, alkaline-earth oxid and metallic sodium, the latter remaining present as such; adding a phenyl-glycin body to such mixture; and then passing the resulting product, while still in fused state, into water out of contact with air.

8. In a method of making indoxyl and its derivatives, the steps which consist in fusing together a phenyl-glycin body with a caustic alkali melt; and then passing the resulting product, while still in fused state, into water.

9. In a method of making indoxyl and its derivatives, the steps which consist in fusing together a phenyl-glycin body with a caustic alkali melt; and then passing the resulting product, while still in fused state, into water, out of contact with air.

10. The method of dissolving indoxyl, which consists in passing the same, while in fused state, into water.

11. The method of dissolving indoxyl, which consists in passing the same, while in fused state, into water, out of contact with air.

Signed by me, this 12 day of June, 1917.

LEE E. H. CONE.